United States Patent [19]

Brown

[11] Patent Number: 5,704,922

[45] Date of Patent: Jan. 6, 1998

[54] SYRINGE HAVING ELECTRICAL CONTACT POINTS FOR METERING DOSES

[75] Inventor: Stephen J. Brown, Mountain View, Calif.

[73] Assignee: Raya Systems, Inc., Mountain View, Calif.

[21] Appl. No.: 591,765

[22] Filed: Jan. 25, 1996

[51] Int. Cl.$^6$ .................................................... A61M 5/00
[52] U.S. Cl. ..................... 604/207; 604/187; 128/DIG. 1
[58] Field of Search ............................ 604/187, 121, 604/189, 207, 208, 218, 246, 117, 118; 128/DIG. 1

[56] References Cited

U.S. PATENT DOCUMENTS

| | | | |
|---|---|---|---|
| 4,950,264 | 8/1990 | Muller | 128/DIG. 1 |
| 5,333,981 | 8/1994 | Mandro et al. | 604/208 |
| 5,449,334 | 9/1995 | Taylor et al. | 604/207 |
| 5,569,212 | 10/1996 | Brown | 604/207 |
| 5,593,390 | 1/1997 | Castellano et al. | 604/187 |

Primary Examiner—Mark Bockelman
Assistant Examiner—A. T. Nguyen
Attorney, Agent, or Firm—Lumen Intellectual Property Services

[57] ABSTRACT

The invention presents a syringe for injecting a dose of an agent and for electrically indicating the size of the dose. The syringe has a barrel for holding the dose and a plunger for expelling the dose from the barrel. The barrel has a conducting rim that contacts a surface of the plunger lined with electrical contact points. The position of the plunger inside the barrel determines which one of the contact points contacts the conducting rim. Each contact point is electrically connected to a different output terminal located on the syringe cap. The conducting rim is electrically connected to a voltage input terminal located on the syringe cap. A voltage applied to the input terminal causes an electric current to flow through a circuit comprising the conducting rim, the one contact point contacting the conducting rim, and the one output terminal connected to that one contact point. The position of the plunger inside the barrel and the size of the dose corresponding to that plunger position are indicated by the one output terminal having the electric current.

14 Claims, 4 Drawing Sheets

SYRINGE HAVING ELECTRICAL CONTACT POINTS FOR METERING DOSES

BACKGROUND—FIELD OF THE INVENTION

The present invention relates to the field of injection syringes, and in particular to an injection syringe having electrical contact points to allow electrical measuring and recording of dose information.

BACKGROUND—DESCRIPTION OF PRIOR ART

Electronic medical records have a significant advantage over paper medical records. With electronic medical records, health care providers and patients can better store, retrieve, and share medical information. Electronic medical records are particularly advantageous for the treatment of chronically ill patients who must self-monitor and self-inject medications on a daily basis. In therapies such as self-administration of insulin, human growth hormone, and other medications, patients themselves perform the injections and keep records.

Typically, the injections of these medications are performed using disposable syringes. Unfortunately, no inexpensive disposable syringe exists that allows electrical measuring and recording of the dose it injects. That is because no existing inexpensive disposable syringe has a mechanism for electrically indicating the size of the dose it contains. As a result, the patient is burdened with the task of manually recording the dose information into a log after performing an injection.

Because of the frequency of such injections, often several times a day for diabetics, it becomes difficult to keep accurate records. Indeed, studies have shown that a patient's own records and recollections are often incomplete and inaccurate. Additionally, patients may intentionally cheat in making their self-recorded entries of dose information in order to create a log book that will please their doctor. In the long-term this makes patient monitoring extremely difficult and jeopardizes the therapy, possibly even endangering the patient's life. Thus, there is a need for an inexpensive disposable syringe that allows objective and accurate electronic recording of dose information.

Attempts have been made at developing syringes that inject predetermined doses. For instance, U.S. Pat. No. 5,009,645 issued to Jules Silver on Apr. 23, 1991 describes a disposable syringe with an adjustable stop mechanism. This mechanism consists of a knife edge which embeds itself into a specified location of a rail section located axially outside the syringe barrel. In this manner the volume of medication to be delivered during the subsequent injection is preset.

Another solution involves a rotatable cap mechanism cooperating with a rotatable plunger. The mechanism for presetting an injection dose in this manner has been described in U.S. Pat. No. 5,104,380 issued to Rury Holman et al. on Apr. 14, 1992 and U.S. Pat. No. 5,226,895 issued to Harris Dale on Jul. 13, 1993. There are also other types of mechanisms for presetting an injection volume in a syringe.

Unfortunately, none of these mechanisms directly address the problem of recording how much medication was injected over the course of a long-term treatment involving a large number of injections. Although the size of the dose can be preset, the patient is still burdened with the task of manually entering the injected dose information into a log. These entries are often unreliable and do not provide an objective and accurate record of the injected dose information.

U.S. Pat. No. 4,853,521 issued to Ronald Claeys on Aug. 1, 1989 presents a programmable, intelligent reader unit which receives and records drug data using hand-held or fixed scanners. The scanners read bar codes in place on syringes, ampules, flow meters, etc. In addition, this intelligent reader allows the user to weigh a syringe before and after injection to determine and record the administered amount of medicine. Dosage data logged in this manner can be displayed or printed out in the form of a record.

While this apparatus comes closest to solving the problem, it involves many complicated steps of weighing syringes, scanning in bar codes, etc. These complex procedures as well as the high cost of the apparatus precludes effective home use. Additionally, the apparatus and barcoded syringes cannot be easily carried by a patient for measuring and injecting doses away from home. Thus, no inexpensive disposable syringe exists that allows dose information to be electrically measured and recorded in an efficient manner. Additionally, no inexpensive disposable syringe exists that allows patients to make an objective and accurate electronic record of dose information.

OBJECTS AND ADVANTAGES OF THE INVENTION

In view of the above, it is an object of the present invention to provide a syringe that allows efficient electrical measuring and recording of the dose it contains. Another object of the invention is to provide a syringe that allows objective and accurate electronic recording of dose information. A further object of the invention is to make the syringe disposable and cost effective.

These and other objects and advantages will become more apparent after consideration of the ensuing description and the accompanying drawings.

SUMMARY OF THE INVENTION

The invention presents a syringe for injecting a dose of an agent and for electrically indicating the size of the dose. The syringe has a barrel for holding the dose and a plunger for expelling the dose from the barrel. The barrel has a conducting rim at one end for conducting electric current. The plunger is inserted into this same end of the barrel so that a surface of the plunger is in contact with the conducting rim.

The surface of the plunger contacting the conducting rim is lined with discrete electrical contact points. These contact points are arranged on the surface of the plunger such that no more than one contact point may contact the conducting rim at the same time. Additionally, the contact points are arranged on the plunger so that the position of the plunger inside the barrel determines which contact point is contacting the conducting rim. The position of the plunger inside the barrel also indicates the size of the dose contained in the syringe. Therefore, the size of the dose contained in the syringe can be determined by determining which contact point is contacting the conducting rim.

To determine which contact point is contacting the conducting rim, the syringe has a number of output terminals electrically connected to the contact points. Each contact point is electrically connected to a different one of the output terminals. Additionally, the syringe has an input terminal electrically connected to the conducting rim. When a voltage is applied to the input terminal, an electric current flows through a circuit comprising the input terminal, the conducting rim, the one contact point contacting the conducting rim, and the one output terminal connected to that one contact point. Because each contact point is connected to a different output terminal, the one output terminal having electric current flow indicates which contact point is contacting the conducting rim, and thus the size of the dose contained in the syringe.

DESCRIPTION

Figure 1:
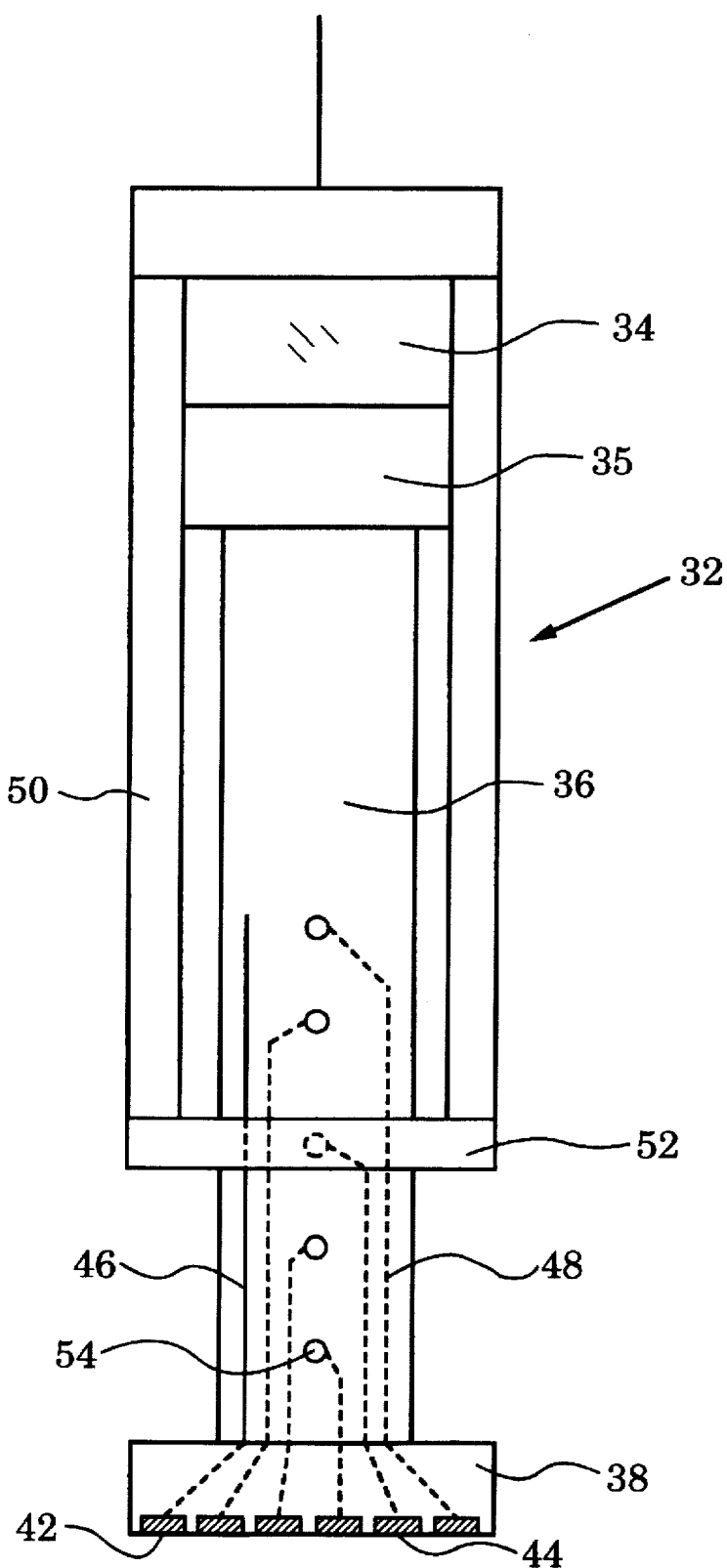
FIG. 1 is a schematic view of a syringe according to the invention.
Figure 2:
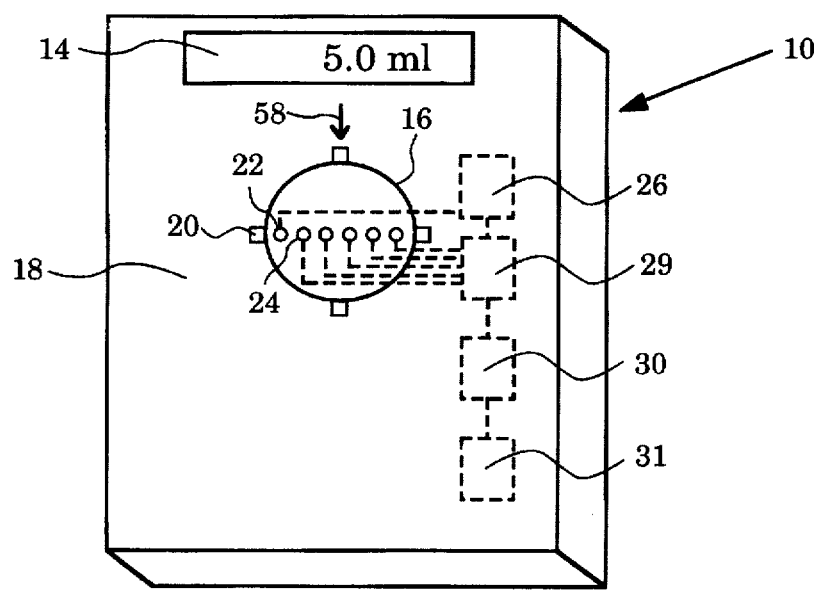
FIG. 2 is a schematic view of a meter for measuring and recording a dose from the syringe of FIG. 1.
Figure 3:
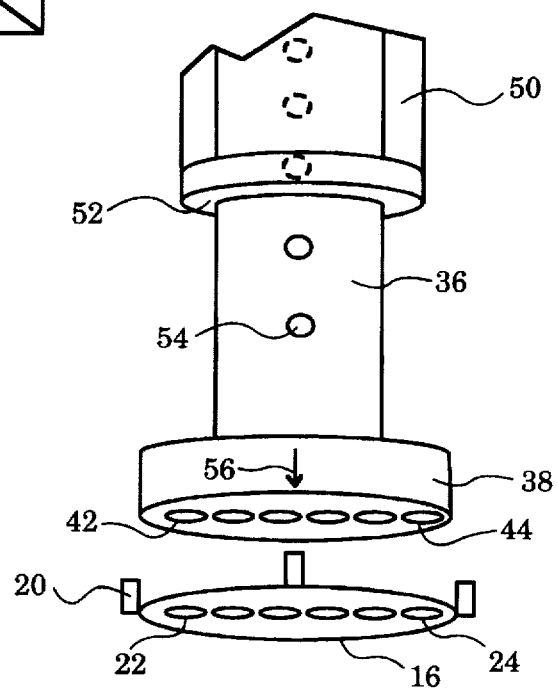
FIG. 3 is a schematic view of the syringe of FIG. 1 being placed on the meter of FIG. 2 for dose measurement.

The preferred embodiment of the invention is illustrated in FIGS. 1-3. Referring to FIG. 1, a syringe 32 has a hollow barrel 50 holding a dose 34 to be injected. A plunger 36 having a piston section 35 is inserted into barrel 50. Dose 34 fills the inner volume of barrel 50 not occupied by plunger 36 and piston 35. The end of plunger 36 not inserted into barrel 50 is attached to a syringe cap 38, such that a force applied on cap 38 in the direction of barrel 50 would cause plunger 36 to advance farther into barrel 50, expelling dose 34 from barrel 50. Barrel 50, plunger 36, piston 35, and cap 38 are made of a non-electrically conductive material, preferably plastic.

The end of barrel 50 through which plunger 36 is inserted has a conducting rim 52. Rim 52 is lined with an electrically conductive material, preferably copper. Some of the conductive material wraps inside barrel 50 such that the conductive material of rim 52 contacts an outer surface of plunger 36. The outer surface of plunger 36 contacting rim 52 is lined with five electrical contact points 54. Contact points 54 are made of an electrically conductive material, preferably copper. In this embodiment, contact points 54 are circular, although other shapes are possible in alternative embodiments.

Contact points 54 are arranged on plunger 36 such that the distance measured along the axis of plunger 36 from the edge of any contact point 54 to the edge of an adjacent contact point 54 is greater than the width of rim 52. This ensures that for any position of plunger 36 inside barrel 50, no more than one contact point 54 may contact rim 52 at the same time. In the preferred embodiment, contact points 54 are located on the outer surface of plunger 36 in a line parallel to the axis of the plunger 36. Also in the preferred embodiment, the distance from each contact point 54 to each adjacent contact point 54 is equal.

Contact points 54 are arranged on the surface of plunger 36 such that the position of plunger 36 inside barrel 50 determines which one contact point 54 contacts rim 52. Because dose 34 fills the volume of barrel 50 not occupied by plunger 36 and piston 35, the position of plunger 36 inside barrel 50 also defines the size of dose 34 contained in barrel 50. Thus, a determination of which one contact point 54 is contacting rim 52 also determines the size of dose 34 contained in barrel 50.

In the preferred embodiment, the contact point 54 closest to cap 38 is located such that it contacts rim 52 when plunger 36 is fully inserted into barrel 50 so that there is no volume available for dose 34 in barrel 50. Thus, this contact point 54 corresponds to a dose size of zero. The contact point 54 third closest to cap 38 is located such that it only contacts rim 52 when plunger 36 has been inserted half way into barrel 50, so that dose 34 fills half of the inner volume of barrel 50. Thus, this contact point 54 corresponds to a dose size equal to half of the inner volume of barrel 50. Similarly, each remaining contact point 54 is located on plunger 36 such that it contacts rim 52 when plunger 36 has a defined position inside barrel 50, and that defined position corresponds to the size of dose 34 contained in barrel 50.

Referring to FIG. 3, cap 38 is a circular disk having a flat outer surface. The outer surface of cap 38 has an input terminal 42 and five output terminals 44. Input terminal 42 and output terminals 44 are made of an electrically conductive material, preferably copper. In the preferred embodiment, input terminal 42 and output terminals 44 are circular in shape and arranged in a straight line along the outer surface of cap 38 such that each terminal is spaced an equal distance from each adjacent terminal. In alternative embodiments, the terminals have different shapes and different arrangements on the surface of cap 38.

Referring again to FIG. 1, five output terminals 44 are electrically connected to five contact points 54 by five output strips 48. Each contact point 54 is electrically connected to a different one of the five output terminals 44. Strips 48 are made of an electrically conductive material, preferably copper wire. In the preferred embodiment, strips 48 are routed from output terminals 44 through cap 38 and along the inside of plunger 36 before connecting to the bottom surface of contact points 54. This ensures that strips 48 do not contact rim 52. In an alternative embodiment, strips 48 are routed from output terminals 44 through cap 38 and molded into the surface of plunger 36 to ensure that strips 48 do not contact rim 52.

Input terminal 42 is electrically connected to rim 52 by an input strip 46. Input strip 46 is connected at one end to input terminal 42, and then routed through cap 38 and along the outer surface of plunger 36, such that input strip 46 contacts rim 52. In the preferred embodiment, input strip 46 extends along the outer surface of plunger 36 in a line parallel to the axis of plunger 36. Input strip 46 extends along the outer surface of plunger 36 a sufficient distance to ensure that input strip 46 contacts rim 52 whenever any one of contact points 54 contacts rim 52.

Referring to FIG. 2, a meter 10 has a placement field 16 delineated on a face plate 18. Placement field 16 is bordered on four sides by rigid positioning studs 20. The dimensions of placement field 16 correspond to the dimensions of cap 38. Face plate 18 has a positioning arrow 58 for indicating the proper orientation of cap 38 on placement field 16. Located inside placement field 16 are five output contacts 24 and an input contact 22. Output contacts 22 and input contact 24 are made of an electrically conductive material, preferably copper.

Input contact 22 is connected to a voltage generator 26 below face plate 18. Voltage generator 26 is thus connected to apply a voltage V to input terminal 42 when input terminal 42 is contacting input contact 22. Typically, the voltage V generated by generator 26 is in the range of 1 to 20 volts, with a preferred value of 9 volts, so that a 9 volt battery could be used as generator 26. A circuit reader 29 is connected to all five output contacts 24 such that it can determine which one output contact 24 has an electric current, as will be described in the operation section below.

A microprocessor 30 is connected to circuit reader 29, such that it can receive the readings of circuit reader 29 regarding which one output contact 24 has an electric current. Microprocessor 30 is programmed to convert the readings of circuit reader 29 into a digital value representative of the size of dose 34. To make this conversion, microprocessor 30 is programmed with the total inner volume capacity of barrel 50, and the inner volume capacity of barrel 50 occupied by plunger 36 and piston 35 when each contact point 54 contacts rim 52. Additionally, microprocessor 30 knows which one of contact points 54 is connected to each output contact 24. An electronic memory 31 is connected to microprocessor 30 such that memory 31 records the digital value representative of the size of dose 34.

FIG. 3 illustrates in detail the positioning of cap 38 on placement field 16 for measurement of dose 34. Cap 38 has a circular outer surface of the same size and shape as placement field 16, such that positioning studs 20 fit exactly around the cap's circumference when cap 38 is placed on placement field 16. Input terminal 42 and five output terminals 44 are located on cap 38 such that when cap 38 is placed on placement field 16 in a correct orientation, input terminal 42 establishes electrical contact with input contact 22 and each of five output terminals 44 establishes electrical contact with a different one of five output contacts 24. Cap 38 has positioning arrow 56 located on its side surface such that when cap 38 is placed on placement field 16 with positioning arrow 56 aligned with positioning arrow 58, the correct orientation of cap 38 on placement field 16 is achieved.

The operation of the preferred embodiment is illustrated in FIGS. 1–3. To perform a measurement and record the size of dose 34, the patient first positions plunger 36 in barrel 50 so that one contact point 54 is contacting rim 52 and so that dose 34 fills the inner volume of barrel 50 not occupied by plunger 36 and piston 35. Before injecting dose 34, the patient places cap 38 of syringe 32 on placement field 16, as shown in FIG. 3. When cap 38 is placed between positioning studs 20 with arrow 56 aligned with arrow 58, input terminal 42 establishes electrical contact with input contact 22 and each of five output terminals 44 establishes electrical contact with a different one of five output contacts 24.

Meanwhile, voltage generator 26 applies voltage V to input contact 22. Voltage V causes an electric current to flow through a circuit comprising input contact 22, input terminal 42, rim 52, the one contact point 54 contacting rim 52, the one output terminal 44 electrically connected to that contact point 54, and the one output contact 24 contacting that one output terminal 44. Circuit reader 29 reads each output contact 24 to determine the one output contact 24 that has the electric current. Circuit reader 29 passes this information to microprocessor 30.

Microprocessor 30 uses the information received from circuit reader 29 to determine the specific contact point 54 contacting rim 52, and thus the specific position of plunger 36 inside barrel 50. Microprocessor 30 then subtracts the inner volume capacity of barrel 50 occupied by plunger 36 and piston 35 from the total inner volume capacity of barrel 50 to calculate the size of dose 34 contained in barrel 50.

Microprocessor 30 produces a digital value representative of the calculated size of dose 34, and records this value in electronic memory 31. The patient then injects dose 34, having already made an electronic record of the dose information. A physician can later review the dosing records stored in electronic memory 31 to assess compliance with the prescribed injection dosing.

Figure 4:
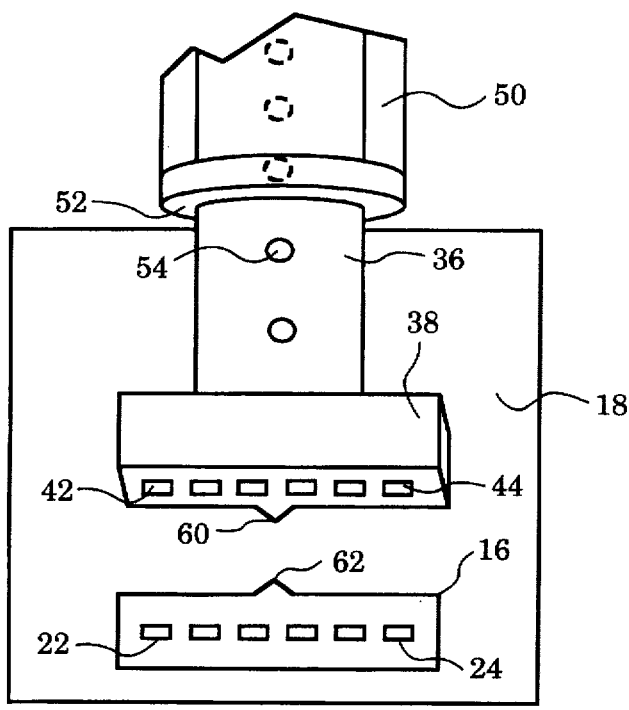
FIG. 4 is a schematic view of another syringe being placed on another meter for dose measurement.

A second embodiment of the invention is shown in FIG. 4. The second embodiment differs from the preferred embodiment in the shapes of cap 38 and placement field 16. Cap 38 is a rectangular box having a tab 60 extending from its outer surface. Placement field 16 has the same size and shape as the outer surface of cap 38 and has a notch 62 of size and shape corresponding to tab 60. Additionally, output contacts 24, input contact 22, output terminals 44, and input terminal 42 now have a rectangular shape.

Input contact 22 and five output contacts 24 are located within placement field 16 such that when cap 38 is placed on placement field 16 in a correct orientation, input terminal 42 establishes electrical contact with input contact 22 and each of five output terminals 44 contacts a different one of five output contacts 24. Tab 60 is located on cap 38 such that when cap 38 is placed on placement field 16 with tab 60 inserted into notch 62, the correct orientation of cap 38 on placement field 16 is achieved.

The operation of the second embodiment differs from the operation of the preferred embodiment in the method of properly orienting cap 38 on placement field 16. Instead of aligning arrows, the user places cap 38 on placement field 16 such that tab 60 is placed into notch 62. Otherwise, the operation and advantages of this embodiment are identical to the operation and advantages of the preferred embodiment described above.

Figure 5:
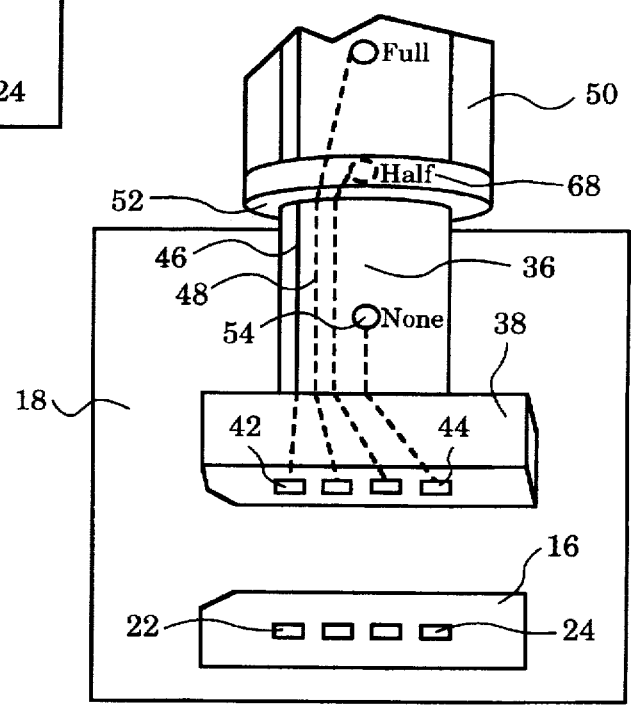
FIG. 5 is a schematic view of another syringe being placed on another meter for dose measurement.

A third embodiment of the invention is shown in FIG. 5. In this embodiment, there are only three contact points 54 and three corresponding output terminals 44. Similarly, placement field 16 has only three output contacts 24 for contacting output terminals 44. This embodiment also illustrates a different method of properly orienting cap 38 on placement field 16. The outer surface of cap 38 and the border of placement field 16 now form unsymmetrical five-sided polygons of equal size. Cap 38 can be placed on placement field 16 in only one orientation that aligns the borders of the outer surface of cap 38 and placement field 16. Input terminal 42 and three output terminals 44 are located on cap 38 such that they establish contact with input contact 22 and three output contacts 24 respectively when cap 38 is placed on placement field 16 in this one orientation.

Each contact point 54 now has an adjacent text field 68 imprinted on the surface of plunger 36. Each text field 68 visually indicates to a patient the size of dose 34 contained in syringe 32 when the contact point 54 adjacent to that text field 68 is contacting rim 52. For example, the text field 68 adjacent to the middle contact point 54 reads "Half", so that a patient filling barrel 50 with an agent knows that the dose size is equal to half the inner volume of barrel 50 when the middle contact point 54 contacts rim 52. Of course, middle contact point 54 is located on plunger 36 such that it contacts rim 52 only when plunger 36 and piston 35 are occupying half of the inner volume capacity of barrel 50.

The operation of the third embodiment differs from the operation of the preferred embodiment in the patient's reading of text field 68 to set a dose 34 to be injected. The patient sets dose 34 by filling barrel 50 with agent until the contact point 54 adjacent to the text field 68 that corresponds to the desired size of dose 34 contacts rim 52. The patient then places cap 38 on placement field 16 in the proper orientation by aligning the border of the outer surface of cap 38 to the border of placement field 16. Otherwise, the operation and advantages of this embodiment are identical to the operation and advantages of the preferred embodiment described above.

Figure 6:
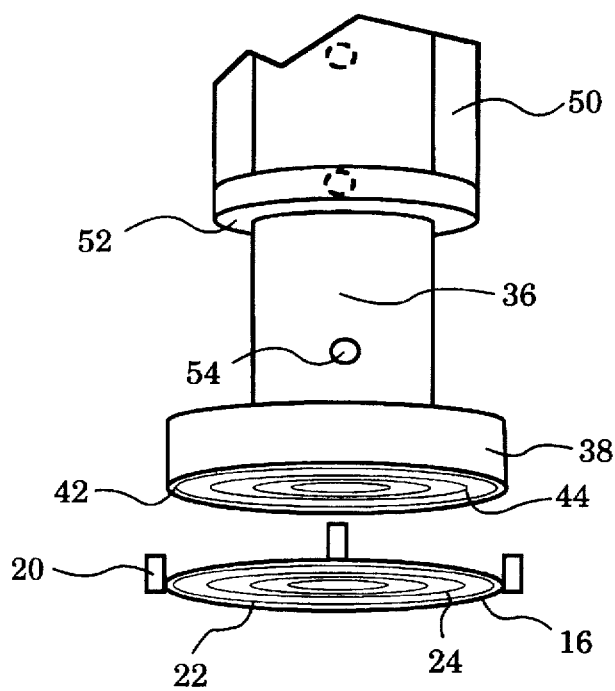
FIG. 6 is a schematic view of another syringe being placed on another meter for dose measurement.
Figure 7:
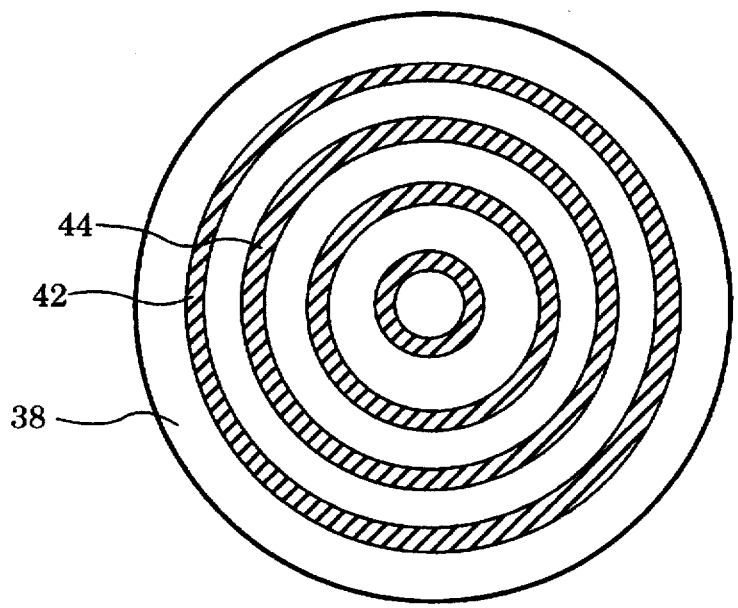
FIG. 7 is a top view of the cap of the syringe of FIG. 6.

A fourth embodiment of the invention illustrating alternative shapes of terminals 42 and 44 is shown in FIG. 6 and FIG. 7. Referring to FIG. 7, input terminal 42 and three output terminals 44 form four concentric circular rings on the outer surface of cap 38. Referring to FIG. 6, placement field 16 is still bordered by four rigid positioning studs 20. However, input contact 22 and three output contacts 24 now form four concentric circular rings within placement field 16. Input terminal 42 and three output terminals 44 are located on the surface of cap 38 such that when cap 38 is placed on placement field 16 between positioning studs 20, input terminal 42 establishes electrical contact with input contact 22, and each of three output terminals 44 establishes electrical contact with a different one of three output contacts 24.

The operation of the fourth embodiment differs from the operation of the third embodiment in the method of placing cap 38 on placement field 16. The patient simply places cap 38 onto placement field 16 between positioning studs 20 without regard to the specific angular orientation of cap 38. Because of the circular ring shapes of input terminal 42, input contact 22, output terminals 44, and output contacts 24, no specific angular orientation of cap 38 on placement field 16 is required. The proper electrical contacts are achieved regardless of the angular orientation of cap 38 on placement field 16. Otherwise, the operation and advantages of this embodiment are identical to the operation and advantages of the third embodiment described above.

SUMMARY, RAMIFICATIONS, AND SCOPE

Although the above description contains many specifities, these should not be construed as limiting the scope of the invention but merely as illustrating some of the presently preferred embodiments. Many other embodiments of the invention are possible. For example, contact points 54 need not be arranged on plunger 36 in a line parallel to the axis of plunger 36. A horizontally staggered arrangement of contact points 54 on the surface of plunger 36 may provide greater visual clarity to a patient.

Additionally, contact points 54 need not be spaced on plunger 36 such that each contact point 54 is an equal distance from each adjacent contact point 54. Unequal spacing of contact points 54 would allow further variation in the sizes of the doses measured. Also, plunger 36 can have a total number of contact points 54 other than the three or five described. Having a different number of contact points 54 on the surface of plunger 36 also allows further variation in the size of doses that can be measured.

Output terminals 44 and input terminal 42 may be located on syringe 32 in locations other than an outer surface of cap 38. Terminal 42 and 44 could be located on an outer surface of barrel 50 or any other location facilitating dose measurement. Additionally, output terminals 44 and input terminal 42 may have sizes and shapes other than those described above. Rim 52 need not be located at an end of barrel 50. Other positions of rim 52 may be equally advantageous for contacting contact points 54. Moreover, cap 38 may be properly positioned on placement field 16 by methods other than those shown.

Therefore, the scope of the invention should be determined, not by examples given, but by the appended claims and their legal equivalents.

I claim:

1. A syringe for injecting a dose of an agent and for electrically indicating the size of said dose, said syringe comprising:
   a) a barrel for holding said dose, said barrel having a conducting rim;
   b) a plunger for expelling said dose from said barrel, said plunger having a surface contacting said conducting rim;
   c) a plurality of contact points arranged on said surface such that no more than one of said contact points contacts said conducting rim at the same time and such that the position of said plunger in said barrel determines which one of said contact points contacts said conducting rim;
   d) a plurality of output terminals electrically connected to said plurality of contact points such that each of said contact points is electrically connected to a different one of said output terminals; and
   e) an input terminal electrically connected to said conducting rim such that a voltage applied to said input terminal causes an electric current to flow through a circuit comprising said input terminal, said conducting rim, one of said contact points contacting said conducting rim, and one of said output terminals electrically connected to said one contact point contacting said conducting rim.

2. The syringe of claim 1, wherein said input terminal and said plurality of output terminals are located on a cap of said syringe.

3. The syringe of claim 2, wherein said cap has a means for indicating a proper orientation of said cap on a placement field of a meter.

4. The syringe of claim 3, wherein said means for indicating a proper orientation comprises an arrow on said cap.

5. The syringe of claim 3, wherein said means for indicating a proper orientation comprises an unsymmetrical shape of said cap and said placement field, such that said cap may be placed on said placement field in only one orientation that aligns the borders of said cap and said placement field.

6. The syringe of claim 3, wherein said means for indicating a proper orientation comprises a tab extending from said cap, said tab being inserted into a notch of said placement field when said cap is placed on said placement field.

7. The syringe of claim 2, wherein said input terminal and said plurality of output terminals comprise concentric circular rings on said cap.

8. The syringe of claim 1, wherein said plurality of contact points are arranged on said surface of said plunger in a line parallel to the axis of said plunger.

9. The syringe of claim 1, wherein said plurality of contact points are arranged on said surface of said plunger such that the distance measured along the axis of said plunger from any one of said contact points to an adjacent contact point is equal.

10. The syringe of claim 1, further comprising indexing means on said plunger for visually indicating the size of said dose contained in said syringe when at least one of said contact points is contacting said conducting rim.

11. The syringe of claim 10, wherein said indexing means comprises a text field imprinted on said plunger adjacent to said at least one contact point.

12. The syringe of claim 1, wherein said input terminal is electrically connected to said conducting rim by an input strip, said input strip being attached to said surface of said plunger such that said input strip contacts said conducting rim.

13. The syringe of claim 1, wherein said plurality of contact points are electrically connected to said plurality of output terminals by a plurality of output strips, said plurality of output strips being routed inside said plunger such that said plurality of output strips do not contact said conducting rim.

14. The syringe of claim 1, wherein said plurality of contact points are electrically connected to said plurality of output terminals by a plurality of output strips, said plurality of output strips being molded into said surface of said plunger such that said plurality of output strips do not contact said conducting rim.

* * * * *